US006306434B1

United States Patent
Hong et al.

(10) Patent No.: US 6,306,434 B1
(45) Date of Patent: Oct. 23, 2001

(54) PHARMACEUTICAL COMPOSITION COMPRISING CYCLOSPORIN SOLID-STATE MICROEMULSION

(75) Inventors: Chung Il Hong, East Amherst, NY (US); Jung Woo Kim; Nam Hee Choi, both of Seoul (KR); Hee Jong Shin; Su Geun Yang, both of Kyeonggi-do (KR); Jae Hyun Kim, Seoul (KR); Jong Lae Lim; Chong Kook Kim, both of Kyeonggi-do (KR)

(73) Assignee: Chong Kun Dang Corp. (KR)

( * ) Notice: Subject to any disclaimer, the term of this patent is extended or adjusted under 35 U.S.C. 154(b) by 0 days.

(21) Appl. No.: 09/555,619

(22) PCT Filed: Dec. 1, 1998

(86) PCT No.: PCT/KR98/00387

§ 371 Date: Jun. 1, 2000

§ 102(e) Date: Jun. 1, 2000

(87) PCT Pub. No.: WO99/27946

PCT Pub. Date: Jun. 10, 1999

(30) Foreign Application Priority Data

Feb. 12, 1997 (KR) .................................................. 97-65420

(51) Int. Cl.[7] .................................................. A61K 9/66
(52) U.S. Cl. .......................... 424/455; 424/451; 424/457; 514/772.3
(58) Field of Search .................................. 424/451, 455, 424/457; 514/772.3

(56) References Cited

U.S. PATENT DOCUMENTS

| | | | |
|---|---|---|---|
| 4,146,499 | 3/1979 | Rosano | 252/186 |
| 5,342,625 | 8/1994 | Hauer et al. | 424/455 |
| 5,447,729 * | 9/1995 | Belenduik | 424/490 |

OTHER PUBLICATIONS

Takada, K. et al., "Enteric Solid Dispersion of Ciclopsorin A (CiA) Having Potential to Deliver CiA inot Lymphatics," Chem. Pharm. Bull., 37:471–474 (1989).*

Takada, K. et al.,"Enteric Solid Dispersion of Ciclosporin A (CiA) Having Potential to Deliver CiA into Lymphatics," Chem. Pharm. Bull., 37:471–474 (1989).

* cited by examiner

Primary Examiner—Thurman K. Page
Assistant Examiner—Rachel M. Bennett
(74) Attorney, Agent, or Firm—Heslin Rothenberg Farley & Mesiti P.C.

(57) ABSTRACT

A pharmaceutical composition comprising a cyclosporin solid-state microemulsion is disclosed. In a preferred embodiment, the composition comprises a cyclosporin microemulsion dispersed in an enteric carrier. The composition does not dissolve in external phases such as artificial gastric fluid, but dissolves rapidly in artificial intestinal fluid, whereby it releases the cyclosporin microemulsion, providing rapid delivery of cyclosporin. The composition effectively maintains a therapeutic blood concentration of cyclosporin with once a day dosing, providing for convenience of administration and avoiding adverse effects induced by increasing peak blood cyclosporin concentrations associated with conventional cyclosporin formulations.

13 Claims, 2 Drawing Sheets

PHARMACEUTICAL COMPOSITION COMPRISING CYCLOSPORIN SOLID-STATE MICROEMULSION

PRIOR FOREIGN APPLICATIONS

This application is a 35 USC §371 filing of International Application Number PCT/KR98/00387, filed Dec. 1, 1998 and claims priority from Korean Patent Application Number 1997/65420, filed Dec. 2, 1997.

TECHNICAL FIELD

The present invention is related to a pharmaceutical composition comprising cyclosporin as an active component. More specifically, the present invention is related to a pharmaceutical composition comprising cyclosporin solid-state microemulsion prepared by dispersing of cyclosporin microemulsion in enteric carrier.

BACKGROUND ART

Cyclosporin is a high molecular peptide compound consisting of 11 amino acids which achieves its potent immunosuppressive activity by inhibiting the growth and differentiation of T cells. There are many cyclosporins such as cyclosporin A, B, C, D, G, etc. depending on the structure of constituent amino acids, but cyclosporin A is preferable used in the clinical field since its pharmacological activity and clinical indication and effectiveness are well established in the art. Cyclosporin is used clinically to prevent allograft rejection after transplantation of tissue or organ such as kidney, liver, heart, bone marrow, pancreas, skin, cornea, etc. And it has been applied to treat autoimmune diseases, especially inflammation disease such as rheumarthritis.

Cyclosporin has a unique structure, which is a cyclic oligopeptide consisting of 11 amino acids. The seven amino acids of cyclosporin are N-methylated. The four remaining protonated nitrogen atoms can form intermolecular hydrogen bonds with carbonyl groups, which contribute substantially to the rigidity, of the cyclosporin skeleton. Therefore, it has a remarkably hydrophobic property, and is relatively insoluble in water (for cyclosporin A. 0.04 mg/ml at 25° C.). Due to such a low water-solubility of cyclosporin, the bioavailability of cyclosporin A is known to be 30% or less. It was reported that the absorption of such an insoluble compound is greatly influenced by bile juice secretions, the amount of fat in food, etc. In the case of cyclosporin A, it has been reported that differences in absorption between individuals are as great as about 5~50%.

10~27% of cyclosporin A absorbed were eliminated by first-pass effect in liver, the half life for distribution of cyclosporin A is 0.7~1.7 h, and the half life for elimination of cyclosporin A is 6.2~23.9 h. The said pharmacological parameters show a large individual difference according to bile juice secretion, the condition of patient transplanted and the kind of transplantation organ.

Even though cyclosporin has almost no bone marrow toxicity unlike other immunosuppressants, it has a very narrow therapeutic range. Nephrotoxicity is the major adverse effect of cyclosporin. Cyclosporin shows adverse effects such as decreasing of glomerular filtration rate, increasing of reabsorption of proximal tubules, etc., dose-dependently. It has been reported that the appearance of an irreversible deterioration of nephron and the inducement of serious nephrotoxicity is a chronic toxicity of cyclosporin multiple dosing.

Therefore, such problems as low bioavailability due to poor aqueous solubility of cyclosporin, individual difference of cyclosporin absorption, narrow therapeutic range, adverse effects showed dose-dependently, etc., must be addressed. And recently, it has come to light that the prevention of adverse effects through a constant maintenance of blood concentration of cyclosporin within the therapeutic range is a difficult but important objective.

In various methods for improvement of nephrotoxicity of cyclosporin, using of prostaglandin derivatives that are antagonists for calcium was tried but it did not show good effect. The risk of the high fluctuation index for rejection and for nephrotoxicity might be mitigated by frequent administration of small doses, thereby maintaining blood concentration of cyclosporin within the therapeutic range. But the administration more than thrice daily is not preferable because cyclosporin usually should be administered for a long period and, in this case, because it is difficult that patient compliance would be high. Therefore, the development of a once a day dosage form of cyclosporin is preferable and expected.

Dosage form development studies of cyclosporin having the said characteristics had been mainly concentrated on the means that are used to solubilize cyclosporin.

The soft gelatin capsule that is commercialized by Sandoz Pharmaceuticals since 1990 can form a crude emulsion in the gastric-instetinal (GI) tract after oral administration. Even though it could produce the great convenience for administration method, it still has the problem that blood concentration of cyclosporin must be monitored frequently. It was because cyclosporin absorption from the said pharmaceutical preparation showed not only large individual difference but also high variability in the same patient depending on food, bile secretion, GI tract function, etc.

Recently, to solve the said problem, a new cyclosporin-preparation using microemulsion system has been developed by Novartis (Sandimmun Neoral). This pharmaceutical preparation shows that cyclosporin bioavailability is almost not affected by food, bile secretion, etc. as well as increasing of its bioavailability. Therefore, frequent monitoring of the trough level of patient is not needed, and hence is a remarkable improvement of pharmaceutical art.

U.S. Pat. No. 4.146,499 disclosed the method using w/o microemulsion using ethanol as a hydrophilic cosurfactant. And U.S. Pat. No. 5.342.625 disclosed the method using non-ethanol component as a hydrophilic cosurfactant to improve the disadvantage of using ethanol.

However, the said cyclosporin microemulsion compositions still have a problem of adverse effects induced by the peak level of blood concentration of cyclosporin. Therefore, a standard dose is administered to all patients initially, and then the blood concentration of cyclosporin must be monitored continuously on each patient. Inconveniently, dose of cyclosporin must be controlled referring to monitoring result, so that allograft rejection and nephrotoxicity would be minimized.

The objective of present invention is the produce of a controlled release preparation that can release cyclosporin for a long time in GI tract after oral administration, while solving the problems of cyclosporin preparations of prior arts.

DISCLOSURE OF INVENTION

The present invention relates to a pharmaceutical composition comprising cyclosporin solid-state microemulsion. Cyclosporin solid-state microemulsion is a solidified product comprising cyclosporin microemulsion and carrier component. More specifically, it can be prepared by dispersing of cyclosporin microemulsion in enteric carrier.

The first essential component of the pharmaceutical composition comprising cyclosporin solid-state microemulsion according to the present invention is cyclosporin microemulsion. A microemulsion comprises two or more immiscible liquid materials together with surfactant like emulsion, but is a thermodynamically stable and optically transparent composition unlike emulsion. And the microemulsion has very low surface tension and small particle size of less than 100 nm, which together result in high absorption and permeation properties of drug delivered by microemulsion. In pharmaceutical composition according to the present invention, any one(s) of conventional cyclosporin microemulsions can be used, but preferable ones are those that do not contain such volatile materials as ethanol, etc. It is because solidifying step is needed in the preparation of cyclosporin solid-state microemulsion.

The terms "cyclosporin microemulsion" and "cyclosporin solid-state microemulsion" used in the present invention are brief expressions for "microemulsion preconcentrate containing cvclosporin" and "solidified product of microemulsion preconcentrate containing cyclosporin". respectively. The terms mean that they can form microemulsion spontaneously after being dissolved in such external phases as water, etc.

The second essential component of the pharmaceutical composition according to the present invention is enteric carrier, which is to be used in the preparation of cyclosporin solid-state microemulsion.

The action of carrier in the pharmaceutical composition according to the present invention is that of serving within the cyclosporin solid-state microemulsion prepared with the said carrier to prevent of the release of cyclosporin in acidic condition, while allowing a rapid release in neural or alkali condition. That is, cyclosporin solid-state microemulsion must not release cyclosporin in the stomach, rather releasing it rapidly in the upper part of the small intestine. Furthermore, the particle size (inner phase diameter) of microemulsion formed in the small intestine must be sufficiently small and, therefore, capable of being maintained at 100 nm or below.

The enteric carriers that can be used in the preparation of cyclosporin solid-state microemulsion are Eudragit® aqueous methacrylic polymers, (Röhm America Inc., Piscataway, N.J., USA) hydroxypropyl methylcellulose phthalate (HPMCP), cellulose acetate phthalate (CAP), sodium alginate, etc. Examples of Eudragit® are Eudragit® L100, Eudragit® S100, Eudragit® RS100, etc. and Eudragit® L100 , aqueous methacrylic acid copolymers, can be used preferably Examples of HPMCP are HPMCP H-50, HPMCP H-55, etc. and HPMCP H-55, which is very soluble in such organic solvent as acetone, can be used preferably. CAP is also useful as an enteric carrier. In the case of using sodium alginate, such additional component as disintegrant is needed additionally because cyclosporin solid-state microemulsion prepared is disintegrated slowly.

In the pharmaceutical composition according to the present invention, one member or mixture of the said carrier materials can be used as a carrier in cyclosporin solid-state microemulsion. And the carrier component may further contain any pharmaceutically acceptable additives as needed. Examples of the said additives include antioxidant, disintegrant, dissolution control agent, flavor, plasticizer, preservatives, coloring agents, etc.

In the pharmaceutical composition according to the present invention, cyclosporin solid-state microemulsion can be prepared preferably with cyclosporin microemulsion and carrier in the range of 1:0.1~3, or more preferably 1:0.2~2 by weight.

The cyclosporin solid-state microemulsion, which is comprised in the pharmaceutical composition of the present invention, can be prepared by any one of methods that can produce the solidified product of the state that cyclosporin microemulsion is dispersed in carrier. A specific example is when cyclosporin microemulsion is added to the solution of carrier, and mixed to be homogeneous. The solvent is then removed by such a method as evaporation under reduced pressure, spray drying etc., resulting in solidification.

The pharmaceutical composition of the present invention may comprise cyclosporin microemulsion together as well as cyclosporin solid-state microemulsion. To maximize the convenience of clinical usage, the pharmaceutical composition containing cyclosporin microemulsion and cyclosporin solid-state microemulsion in the proper mixing ratio can be selected, prepared in the proper dosage form (for example, the pharmaceutical composition is filled in soft capsule or hard capsule), and then used. In the pharmaceutical composition of the present invention, the mixing ratio of cyclosporin microemulsion and cyclosporin solid-state microemulsion is preferably in the range of 1:0.1~5, or more preferably 1:0.5~2 by weight.

Moreover, cyclosporin microemulsion and cyclosporin solid-state microemulsion, comprised in the pharmaceutical composition of the present invention, can be prepared also in the pharmaceutical preparations independently from one another, and then administered. For example, they can be filled in soft capsule and hard capsule, respectively, and then administered together.

The pharmaceutical composition according to the present invention is characterized in that it does not dissolve in such external phases as water and artificial gastric fluid but dissolves in artificial intestinal fluid, thereby getting the microemulsion form. And by varying the mixing ratio of the components, the inner phase diameter of the microemulsion formed can be controlled easily to be 100 nm or below.

The pharmaceutical composition of the present invention, which is prepared according to the said descriptions, can maintain the blood concentration of cyclosporin within therapeutic range for about 1 day through only one dosing per day. Furthermore, it can avoid such adverse effects of cyclosporin as nephrotoxicity, etc. that originate from the high blood cyclosporin concentration.

BRIEF DESCRIPTION OF THE DRAWINGS

For a thorough understanding of the nature and objects of the invention, reference should be noted according to the following detailed description taken in connection with the accompanying drawings in which.

MODES FOR CARRYING OUT THE INVENTION

Figure 1:
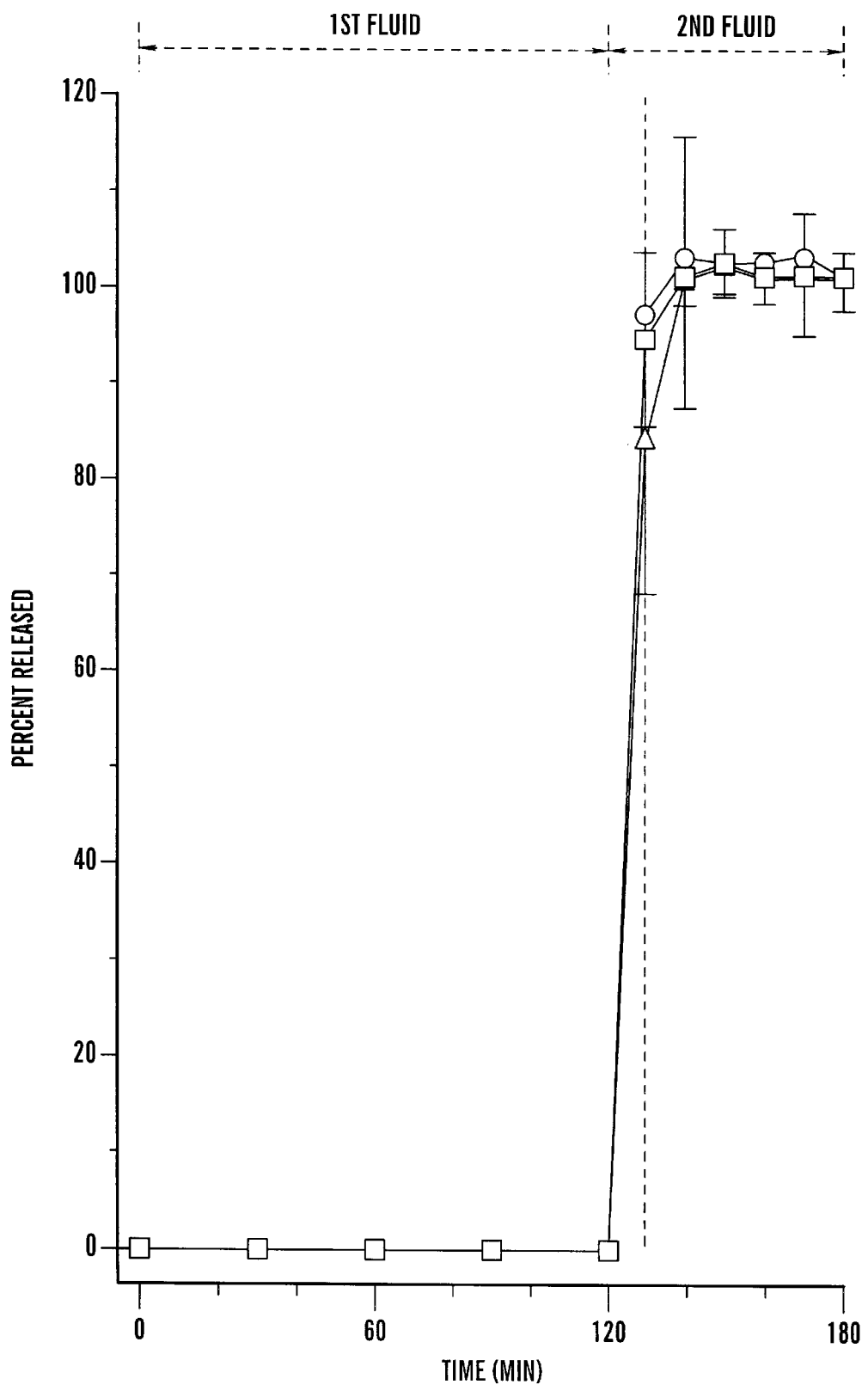
FIG. 1 shows release of cyclosporin solid-state microemulsions prepared using various different ratios Eudragit® L100 to cyclosporin microemulsion. Key: ○, Experimental example 1-A; △, Experimental example 1-B; and □, Experimental example 1-C.
Figure 2:
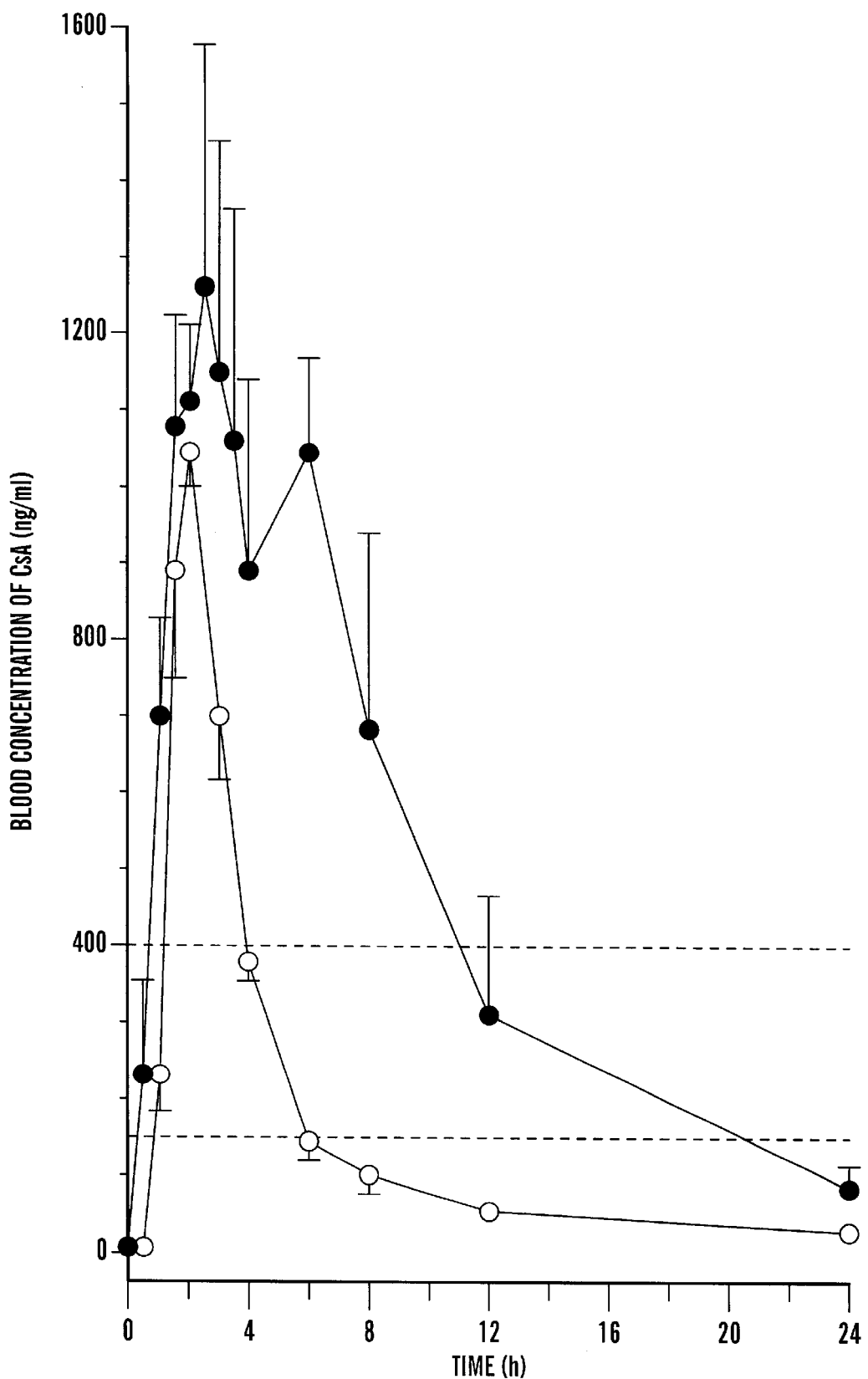
FIG. 2 shows the mean blood cyclosporin concentrations following the single oral administration of cyclosporin microemulsion (○) (equivalent to 100 mg of cyclosporin A) to dogs and following the single oral combination administration (●) of cyclosporin microemulsion (equivalent to 100 mg of cyclosporin A) and cyclosporin solid-state microemulsion cyclosporin (equivalent to 100 mg of cyclosporin A) to dogs.

The present invention is described in more detail by the Examples and Experiment as shown below but is not restricted to them.

EXAMPLE 1

50 g of Eudragzit® L100, as an enteric carrier, was dissolved completely in acetone. 50 g of cyclosporin microemulsion prepared with the composition of Table 1 was added into the carrier solution and mixed homogeneousiny. The solution was then evaporated slowly at 30~60° C. under reduced pressure to remove the solvent completely. Cyclosporin solid-state microemulsion film produced was powdered, and formulated into pharmaceutical preparations, that is, capsule, powder, granule and tablet according to conventional methods.

TABLE 1

| Components | Amount per one dose (mg) |
|---|---|
| Cyclosporin A | 100 |
| Medium chain triglyceride | 185 |
| Cremophor RH 40 | 365 |
| Mono- and di-glyceride | 72.5 |
| Poloxamer 124 | 72.5 |
| Propylene carbonate | 205 |

EXAMPLE 2

The pharmaceutical preparations comprising cyclosporin solid-state microemulsion were prepared in the same manner as Example 1 except using HPMCP instead of Eudragit® L100.

EXAMPLE 3

The pharmaceutical preparations comprising cyclosporin solid-state microemulsion were prepared in the same manner as Example 1 except using CAP instead of Eudragit® L100.

EXAMPLE 4

10 g of sodium alginate, as an enteric carrier, was dissolved completely in water thereby to be 2% aqueous solution, 50 g of cyclosporin microemulsion prepared with the composition of Table 1 was added into the carrier solution and mixed homogeneously. The solution was then dropwised into 0.2M calcium chloride solution to produce alginate beads. The alginate beads comprising cyclosporin microemulsion were separated and dried. Cyclosporin solid-state microemulsion produced was powdered, and formulated into pharmaceutical preparations, that is, capsule, powder, granule and tablet according to conventional methods.

EXAMPLE 5

The pharmaceutical preparations comprising cyclosporin solid-state microemulsion were prepared in the same manner as Example 4 except additionally using polyethylene oxide of 5 g as a dissolution control agent.

EXAMPLE 6

50 g of cyclosporin microemulsion prepared with the composition of Table 1 was mixed with 100 g of the powder of cyclosporin solid-state microemulsion prepared in Example 1. And the resulting composition was poured to a machine for preparing soft capsules and then encapsulated according to conventional methods for producing soft capsules. Each capsules contained 100 mg of cyclosporin A.

EXAMPLE 7

With 100 g of the powder of cyclosporin solid-state microemulsion prepared in Example 1, 50 g of cyclosporin microemulsion prepared with proper composition was mixed. And the resulting composition was filled in hard gelatin capsules. The conjugated portion of the hard capsules was sealed with gelatin banding to produce hard capsules containing 100 mg of cyclosporin A per capsule.

EXAMPLE 8~14

The pharmaceutical preparations comprising cyclosporin solid-state microemulsion were prepared in the same manner as Example 1~7 except using cyclosporin microemulsion of Table 2 instead of one of Table 1.

TABLE 2

| Components | Amount per one dose (mg) |
|---|---|
| Cyclosporin A | 100 |
| 1,2-Propylene glycol | 75 |
| Ethanol | 150 |
| Refined trans-esterification products of corn oil and glycerol (MAISINE) | 345 |
| Cremophor RM 40 | 405 |

EXAMPLE 15~21

The pharmaceutical preparations comprising cyclosporin solid-state microemulsion were prepared in the same manner as Example 1~7 except using cyclosporin microemulsion of Table 3 instead of one of Table 1.

TABLE 3

| Components | Amount per one dose (mg) |
|---|---|
| Cyclosporin A | 100 |
| Triacetin | 210 |
| Cremophor RH40 | 430 |
| Tween 20 | 70 |
| Cremophor EL | 70 |
| Poloxamer 124 | 70 |
| Linoleic acid | 115 |
| Labrafac CC | 285 |

The cyclosporin solid-state microemulsion in the pharmaceutical composition of the present invention was designed that it does not release cyclosporin in acidic condition, but can release rapidly in neutral or alkali condition. Therefore, the release test and the absorption test in dogs were performed to prove the characteristics designed.

Experimental Example 1

Release Test

Test sample preparation 1-A was prepared as follows:

50 g of Eudragit® L100, as an enteric carrier, was dissolved completely in acetone, 50 g of cyclosporin microemulsion prepared with the composition of Table 1 was added into the carrier solution and mixed homogeneously. The solution was then evaporated slowly at 30~60° C. under reduced pressure to remove the solvent completely. Cyclosporin solid-state microemulsion film produced was powdered, and filled in hard capsules to contain 50 mg of cyclosporin A per capsule. The conjugated portion of the hard capsules was sealed with gelatin banding.

Test samples 1-B and 1-C were prepared in the same manner with test sample preparation 1-A except amount of Eudragit® L100 used, demonstrated in Table 4.

TABLE 4

| Components | Amount used for preparation of cyclosporin solid-state microemulsion (g/batch) | | |
|---|---|---|---|
| | Experimental example 1-A | Experimental example 1-B | Experimental example 1-C |
| Cyclosporin microemulsion | 50 | 50 | 50 |
| Eudragit ® L100 | 50 | 75 | 100 |

The release test was performed according to USP XXIII dissolution apparatus II procedure. The paddle was set at the level of 2.5-cm distance from the bottom of the vessel. Samples equivalent to 100 mg of cyclosporin A encapsulated in hard gelatin capsule was loaded in 500 ml of simulated gastric fluid (pH 1.2) (1st fluid) at 37.0±0.5° C. with stirring speed of 100 rpm. Each sample (4 ml) was withdrawn at 0, 30, 60, 90 and 120 min with compensation of equal volume of dissolution medium.

After completion of release test in the simulated gastric fluid for 120 min, 400 ml of 0.235 M sodium phosphate monobasic solution was immediately added into the vessel to adjust pH 6.8 (2nd fluid). Aliquots (4 ml) of the sample were taken at 10, 20, 30, 40, 50 and 60 min with compensation of equal volume of the mixture (5:4) of simulated gastric fluid and 0.235 M sodium phosphate monobasic solution.

The cyclosporin A concentrations of the samples were determined by HPLC (high-performance liquid chromatography) at the following condition:

HPLC - - - system Hewlet Packard (USA)

Column - - - Capselipak $C_{18}$

Mobile phase - - - Acetonitrile:Methanol:Phosphoric acid buffer [65:5:30 ]

Flow rate - - - 2.0 ml/min

Detector wavelength - - - 215 nm.

The result of the release test was shown in FIG. 1. The cyclosporin solid-state microemulsion in the pharmaceutical composition of the present invention was stable in simulated gastric fluid and then released cyclosporin in simulated intestinal fluid rapidly and completely.

Experimental Example 2

Absorption Test in Dogs

Ten male dogs, weighing 15=2 kg, were used, and each groups consisted of five dogs. No food, only water was supplied to dogs for 18 h prior to drug administration. Test sample preparation 1-A (cyclosporin solid-state microemulsioni) and soft capsule of Table 1 (cyclosporin microemulsion) were administered to dogs in a combination manner with dose of cyclosporin A 100 mg per dog per pharmaceutical preparation, and then 30~40 ml of water was administered immediately. After 4 h from drug administration, food was provided. Venous blood samples of 3 ml was withdrawn in the cephalic vein before drug administration for baseline cyclosporin A levels, and at schedule time intervals, that is 0.5, 1, 1.5, 2, 2.5, 3, 3.5, 4, 6, 8 and 12 h, after dosing. Blood samples were frozen under −18° C. until assay,. Blood concentrations of cyclosporin A were analyzed by RIA (radioimmunoassay) method.

The dog-whole blood cyclosporin A concentration vs. time curves of each preparation are presented in FIG. 1. it shows that administration of the pharmaceutical composition comprising cyclosporin microemulsion and cyclosporin solid-state microemulsion according to the present invention could maintain trough level above the lower limit of therapeutic range for about 24 h without additional increase of peak blood level.

In conclusion, the pharmaceutical composition of the present invention, which comprises a solidified product of cyclosporin microemulsion of prior arts, can maintain the blood concentration of cyclosporin A within therapeutic range for about 1 day through only one dosing per day. Therefore, it is possible to avoid the adverse effects, such as nephrotoxicity, etc., induced by the additional increasing of the peak level of blood cyclosporin concentration in the conventional cyclosporin preparation, and furthermore, a convenience for administration can be obtained.

What is claimed is:

1. A cyclosporin solid-state microemulsion comprising a solidified product consisting essentially of a cyclosporin microemulsion dispersed in an enteric carrier.

2. A pharmaceutical composition according to claim 1, wherein the cyclosporin is cyclosporin A.

3. A pharmaceutical composition according to claim 1, wherein the carrier comprises one or more enteric polymer materials.

4. A pharmaceutical composition according to claim 3, wherein the one or more enteric polymer materials are chosen from the group consisting of aqueous methacrylic polymers, hydroxypropyl methylcellulose phthalates, cellulose acetate phthalate and sodium alginate.

5. A pharmaceutical composition according to claim 4, wherein the aqueous methacrylic polymers are aqueous methacrylic acid copolymers.

6. A pharmaceutical composition according to claim 1, wherein the cyclosporin microemulsion and the carrier are present in a mixing ratio of 1:0.1~3 by weight.

7. A pharmaceutical composition comprising a cyclosporin microemulsion and a cyclosporin solid-state microemulsion according to claim 1.

8. A pharmaceutical composition according to claim 7, wherein the cyclosporin microemulsion and the cyclosporin solid-state microemulsion are present in a mixing ratio of 1:0.1~5 by weight.

9. A pharmaceutical composition according to claim 8, wherein the cyclosporin microemulsion and the cyclosporin solid-state microemulsion are present in a mixing ration of 1:0.5~2 by weight.

10. A pharmaceutical formulation in the form of a soft or hard capsule containing a pharmaceutical composition according to claim 7.

11. A pharmaceutical composition according to claim 3, wherein the cyclosporin microemulsion and the carrier are present in a mixing ratio of 1:0.1~3 by weight.

12. A pharmaceutical composition according to claim 4, wherein the cyclosporin microemulsion and the carrier are present in a mixing ratio of 1:0.1~3 by weight.

13. A pharmaceutical composition according to claim 5, wherein the cyclosporin microemulsion and the carrier are present in a mixing ratio of 1:0.1~3 by weight.

* * * * *